United States Patent [19]

Schütz et al.

[11] Patent Number: 4,876,341

[45] Date of Patent: Oct. 24, 1989

[54] PROCESS FOR THE PREPARATION OF 6-METHYL-3,4-DIHYDRO-1,2,3-OXATHIAZIN-4-ONE 2,2-DIOXIDE

[75] Inventors: Joachim Schütz, Hofheim am Taunus; Otto E. Schweikert, Kelkheim, both of Fed. Rep. of Germany

[73] Assignee: Hoechst Aktiengesellschaft, Frankfurt am Main, Fed. Rep. of Germany

[21] Appl. No.: 227,465

[22] Filed: Aug. 2, 1988

Related U.S. Application Data

[63] Continuation of Ser. No. 890,491, Jul. 25, 1986, abandoned.

[30] Foreign Application Priority Data

Jul. 29, 1985 [DE] Fed. Rep. of Germany ....... 3527070

[51] Int. Cl.$^4$ .......................................... C07D 291/06
[52] U.S. Cl. ........................................ 544/2
[58] Field of Search ............................. 544/2

[56] References Cited

U.S. PATENT DOCUMENTS 4,563,521 1/1986 Clauss et al. ........................... 544/2
4,607,100 8/1986 Clauss et al. ........................... 544/2
4,638,063 1/1987 Clauss et al. ........................... 544/2

FOREIGN PATENT DOCUMENTS 2453063 5/1976 Fed. Rep. of Germany .

OTHER PUBLICATIONS

Clauss et al., Angewandte Chemie, vol. 12, No. 11, International Edition, pp. 869–876 (1973).
Petersen, Ber., vol. 83, pp. 551–558 (1950).

Primary Examiner—John M. Ford
Attorney, Agent, or Firm—Curtis, Morris & Safford

[57] ABSTRACT

Acetoacetamide-N-sulfonic acid and its salts are cyclized with at least approximately the equimolar amount of $SO_3$ in short times, preferably in special apparatus, to give 6-methyl-3,4-dihydro-1,2,3-oxathiazin-4-one 2,2-dioxide. In the case where more than the equimolar amount of $SO_3$ is used, the latter compound is produced as an $SO_3$ adduct which then needs to be hydrolyzed; the hydrolysis also takes place in short times and, particularly advantageously, in apparatus of the same type as for the cyclization.

The non-toxic salts, especially the potassium salt - of 6-methyl-3,4-dihydro-1,2,3-oxathiazin-4-one 2,2-dioxide are valuable synthetic sweeteners.

20 Claims, 2 Drawing Sheets

PROCESS FOR THE PREPARATION OF 6-METHYL-3,4-DIHYDRO-1,2,3-OXATHIAZIN-4-ONE 2,2-DIOXIDE

This application is a continuation of application Ser. No. 890,491, filed 7/25/86, now abandoned.

6-methyl-3,4-dihydro-1,2,3-oxathiazin-4-one 2,2-dioxide is the compound of the formula As a consequence of the acidic hydrogen on the nitrogen atom, the compound is able to form salts (with bases). The non-toxic salts such as, for example, the Na, K and Ca salt can be used as sweeteners in the foodstuffs sector, because some of them have an intensely sweet taste, the K salt ("Acesulfame K" or just "Acesulfame") being of particular importance.

A number of different processes is known for the preparation of 6-methyl-3,4-dihydro-1,2,3-oxathiazin-4-one 2,2-dioxide and its non-toxic salts; cf. Angewandte Chemie 85, No. 22 (1973), pages 965 to 73, corresponding to International Edition Vol. 12, No. 11 (1973), pages 869–76. Virtually all the processes start from chlorosulfonyl or fluorosulfonyl isocyanate ($XSO_2NCO$ with $X=Cl$ or $F$). The chlorosulfonyl or fluorosulfonyl isocyanate is then reacted with monomethyl acetylene, acetone, acetoacetic acid, tert.-butyl acetoacetate or benzyl propenyl ether (usually in a multistage reaction) to give acetoacetamide-N-sulfonyl chloride or fluoride, which cyclizes under the action of bases (such as, for example, methanolic KOH), and provides the corresponding salts of 6-methyl-3,4-dihydro-1,2,3-oxathiazin-4-one 2,2-dioxide. The free oxathiazinone can, if desired, be obtained from the salts in a customary manner (with acids).

Another process for the preparation of the oxathiazinone intermediate acetoacetamide-N-sulfonyl fluoride starts from amidosulfonyl fluoride $H_2NSO_2F$, the partial hydrolysis product of fluorosulfonyl isocyanate (German Offenlegungsschrift 2,453,063). The fluoride of amidosulfonic acid $H_2NSO_2F$ is then reacted with approximately an equimolar amount of the acetoacetylating agent diketene in an inert organic solvent in the presence of an amine at temperatures between about $-30$ and $100°$ C.; the reaction takes place in accordance with the following reaction equation (with triethylamine as the amine):

acetoacetamide-N-sulfonyl fluoride

The acetoacetamide-N-sulfonyl fluoride is then cyclized using a base in a customary manner, for example using methanolic KOH, to the sweetener:

"Acesulfame"

Although the known processes provide, in some instances, quite satisfactory yields of 6-methyl-3,4-dihydro1,2,3-oxthiazin-4-one 2,2-dioxide and its non-toxic salts (up to about 85% of theory based on the starting amidosulfonyl halide), they are still in need of improvement, especially for industrial purposes, because of the necessity of using the not very readily accessible starting materials chlorosulfonyl or fluorosulfonyl isocyanate; this is because the preparation of the chlorosulfonyl and fluorosulfonyl isocyanate requires, because some of the starting materials are rather unpleasant to manipulate (HCN, $Cl_2$, $SO_3$ and HF), considerable precautionary measures and safety arrangements. The preparation of the chlorosulfonyl and fluorosulfonyl isocyanates is based on the following reaction equations:

$HCN + Cl_2 \rightarrow ClCN + HCl$

$ClCN + SO_3 \rightarrow ClSO_2NCO$ $ClSO_2NCO + HF \rightarrow FSO_2NCO + HCl$ Replacement of amidosulfonyl fluoride in the process of the abovementioned German Offenlegungsschrift No. 2,453,063 by, for example, the considerably more easily obtainable (for example from NH₃+SO₃) amidosulfonic acid $H_2NSO_3H$ or its salts hardly appeared promising because of the fact that the reaction of Na amidosulfonate $H_2NSO_3Na$ with diketene in aqueous alkaline solution results in absolutely no reaction product which can be isolated pure. On the contrary, it has been possible to obtain the 1:1 adduct, which there is no doubt is one of the products of this reaction, only in the form of the coupling product with 4-nitrophenyldiazonium chloride as a pale-yellow dyestuff; cf Ber. 83 (1950), pages 551-558, in particular page 555, last paragraph before the description of the experiments, and page 558, last paragraph:

Moreover, acetoacetamide-N-sulfonic acid has otherwise been postulated only or also as an intermediate in the decomposition of 6-methyl-3,4-dihydro-1,2,3-oxathiazin-4-one 2,2-dioxide on boiling in aqueous solution; cf. the literature cited initially, Angew. Chemie (1973) op. cit.:

Thus, because the processes of the state of the art for the preparation of 6-methyl-3,4-dihydro-1,2,3-oxathiazin-4-one 2,2-dioxide and its non-toxic salts are not entirely satisfactory, especially for being carried out on the industrial scale, particularly because of the necessity to use starting materials which are not very straightforward to obtain, the object was to improve the known processes appropriately or to develop a new and improved process.

To achieve this object is has already been proposed that the process of German Offenlegungsschrift No. 2,453,063 be modified, mainly in such a way that the amidosulfonyl fluoride in the known process is replaced by salts of amidosulfonic acid, and the ring closure of the resulting product of acetoacetylation is then carried out using SO₃ (U.S. application Ser. No. 714,177 filed Mar. 20, 1985 - HOE 84/F 064).

The last-mentioned patent application relates specifically to a process for the preparation of 6-methyl-3,4-dihydro-1,2,3-oxathiazin-4-one 2,2-dioxide and its non-toxic salts by (a) reaction of an amidosulfonic acid derivative with at least an approximately equimolar amount of an acetoacetylating agent in an inert organic solvent, where appropriate in the presence of an amine or phosphine catalyst, to give an acetoacetamide derivative, and

(b) ring closure of the acetoacetamide derivative; the process comprises use as the amidosulfonic acid derivative in step (a) of a salt of amidosulfonic acid which is at least partially soluble in the inert organic solvent which is used, and comprises ring closure of the acetoacetamide-N-sulfonate formed in this step, or of the free acetoacetamide-N-sulfonic acid, in step (b) to give 6-methyl-3,4-dihydro-1,2,3-oxathiazin-4-one 2,2-dioxide by the action of at least approximately the equimolar amount of SO₃, where appropriate in an inert inorganic or organic solvent, and comprises the product which results in this case in the acid form then, where appropriate, in a step (c) also being neutralized with a base.

The reaction equations on which the process is based are given in the abovementioned patent application as follows (with diketene as acetoacetylating agent):

-continued (b)

+ SO₃ ⟶

+ MHSO₄

(c)

+ M'OH ⟶

+ H₂O (M' = cation of base)

In this diagram step (b) is shown with the amount of SO₃ being equimolar to that of the acetoacetamide-N-sulfonate. However, it is preferable to use an excess of SO₃. This results in an intermediate whose chemical structure is not as yet accurately known but which is possibly an SO₃ adduct of 6-methyl-3,4-dihydro-1,2,3-oxathiazin-4-one 2,2-dioxide - called "SO₃ adduct" below - and which then has to be hydrolyzed. Thus, in this case, the abovementioned reaction step (b) comprises two part-steps, namely b1: Ring closure

+ n SO₃ ⟶

(n > 1)

-continued

+ MHSO₄

"SO₃ adduct"

b2: Hydrolysis

+ (n − 1)H₂O ⟶

+ (n − 1)H₂SO₄

The reaction temperatures mentioned for the ring closure reaction (b1) in the abovementioned patent application are temperatures between about −70° and +175° C., preferably between about −40° and +10° C. The examples relating to reaction step (b) mostly take place at temperatures between about −30° and −25° C.

The reaction times are said to be "up to about 10 hours"; no lower limit is stated. In all the examples relating to reaction step (b) the reaction times for the ring closure reaction are longer than one hour; all the examples were carried out in standard vessels and with stirring.

The hydrolysis (b2) following the ring closure reaction is carried out by addition of water or ice. The abovementioned patent application contains no specific data on the temperature and the reaction time for the hydrolysis.

For the other process details, reference may be made to the detailed description in the abovementioned patent application.

The process starts from readily obtainable and reasonably priced starting materials and can be carried out extremely straightforwardly. The yields are:

in step (a) about 90 to 100% of theory (based on the starting amidosulfonate), in step (b) about 70 to 95% of theory (based on the acetoacetamide-N-sulfonate), and in step (c) about 100% of theory (based on the oxathiazinone in the acid form), so that the resulting yields for the overall process are between about 65 and 95% of theory.

During the course of further work on this process it has now been found that both the ring closure reaction (b1) and the hydrolysis (b2) take place in extremely short times; thus it is possible considerably to improve the industrial procedure for and, in particular, the space-time yield of the process.

Thus the invention relates to a process for the preparation of 6-methyl-3,4-dihydro-1,2,3-oxathiazin-4-one 2,2-dioxide by ring closure of an acetoacetamide derivative; the process comprises use as an acetoacetamide derivative of acetoacetamide-N-sulfonic acid or its salts - dissolved in an inert solvent—and comprises the ring closure being carried out by the action of at least approximately an equimolar amount of SO₃—where appropriate likewise dissolved in an inert solvent—in a time not exceeding about 10 minutes, and comprises, in the case where more than the equimolar amount of SO₃ is used, the 6-methyl-3,4-dihydro-1,2,3-oxathiazin-4-one 2,2-dioxide which results as the SO₃ adduct then being hydrolyzed.

It is very surprising that ring closure of acetoacetamide-N-sulfonic acid and its salts takes place very smoothly with SO₃ because of the fact that the elimination of water or base occurring during the ring closure does not take place, or virtually does not take place, with other agents eliminating water or bases, such as, for example, P₂O₅, acetic anhydride, trifluoroacetic anhydride, thionyl chloride etc., as it has already been possible to show in the abovementioned patent application by means of a comparison example (with P₂O₅).

Furthermore, the completion of the reaction in short or very short times is also completely surprising.

Because of the short reaction time and the great evolution of heat high yields are achieved preferably in special apparatus. Preferred hold-up times are between about 0.001 and 60 seconds, in particular between about 0.01 and 10 seconds.

The preparation of the starting acetoacetamide-N-sulfonic acid and of its salts is preferably carried out in accordance with step (a) of the process of the abovementioned patent application by reaction of the Li or ammonium salts of the amidosulfonic acid with diketene in inert organic solvents. This entails solutions of the Li and ammonium salts of acetoacetamide-N-sulfonic acid being obtained, which can directly be used as such for the ring closure reaction with SO₃.

Of course, it is also possible to use other salts of acetoacetamide-N-sulfonic acid for the abovementioned ring closure reaction—in particular alkali metal and alkaline earth metal salts. The use of free acetoacetamide-N-sulfonic acid entails no advantages over the salts.

Suitable inert solvents for dissolving the acetoacetamide-N-sulfonic acid or its salts are mainly those inert organic solvents which are specified in the abovementioned patent application as solvents for carrying out step (a) of the process in that patent; hence they are halogenated aliphatic hydrocarbons, preferably those having up to four carbon atom such as, for example, methylene chloride, chloroform, 1,2-dichloroethane, trichloroethylene, tetrachloroethylene, trichlorofluoroethylene etc.;

aliphatic ketones, preferably those having 3 to 6 carbon atoms, such as, for example, acetone, methyl ethyl ketone etc.;

aliphatic ethers, preferably cyclic aliphatic ethers having 4 or 5 carbon atoms such as, for example, tetrahydrofuran, dioxane etc.;

lower aliphatic carboxylic acids, preferably those having 2 to 6 carbon atoms such as, for example, acetic acid, propionic acid etc.;

aliphatic nitriles, preferably acetonitrile;

N-alkyl-substituted amides of carbonic acid and lower aliphatic carboxylic acids, preferably amides having up to 5 carbon atoms such as, for example, tetramethylurea, dimethylformamide, dimethylacetamide, N-methylpyrrolidone, etc.;

aliphatic sulfoxides, preferably dimethyl sulfoxide, and aliphatic sulfones, preferably sulfolane Solvents from the above list which are particularly preferred are methylene chloride, 1,2-dichloroethane, acetone, glacial acetic acid and dimethylformamide, especially methylene chloride.

The solvents can be used both alone and in a mixture.

The concentration of the acetoacetamide-N-sulfonic acid or of its salts in the inert solvent is not crucial but is limited on the one hand by the solubility and on the other hand by economic considerations, since with a high dilution a large amount of solvent subsequently has to be removed again and worked up. In general, concentrations between about 0.1 and 2 mole of acetoacetamide-N-sulfonic acid or of its salts per liter are appropriate.

SO₃ can be used in the form of the gas or in liquid or dissolved form. Suitable solvents for the SO₃ are the inorganic and organic solvents specified in the description of step (b) of the process of the abovementioned patent application; hence they are inorganic solvent: liquid SO₂;

organic solvents: halogenated aliphatic hydrocarbons, preferably having up to four carbon atoms such as, for example, methylene chloride, chloroform, 1,2-dichloroethane, trichloroethylene, tetrachloroethylene, trichlorofluoroethylene etc.

carbonic esters with lower aliphatic alcohols, preferably with methanol or ethanol;

nitroalkanes, preferably having up to four carbon atoms, in particular nitromethane;

alkyl-substituted pyridines, preferably collidine; and aliphatic sulfones, preferably sulfolane.

The organic solvents can be used both alone and in a mixture.

Particularly preferred solvents are liquid SO₂ and methylene chloride.

The amount of the inert solvent which is used is not crucial. If a solvent is used, it is merely necessary to ensure adequate dissolution of the reactants; the upper limit of the amount of solvent is determined by economic considerations. Favorable concentrations are about 5 to 50% by weight, preferably about 15 to 30% by weight, of SO₃.

In a preferred embodiment of the process according to the invention the same inert solvent is used both for the acetoacetamide-N-sulfonic acid or its salts and for the SO₃, preferably one from the group of halogenated aliphatic hydrocarbons, in particular only methylene chloride.

Concerning the molar ratio of acetoacetamide-N-sulfonic acid or -sulfonate and SO₃, in principle the statement which applies is the same as that relating to step (b) of the process of the abovementioned patent application. Thus, the molar ratio can in fact be about 1:1, but an excess of SO₃ of up to about 20-fold is preferred, preferably an approximately 3- to 10-fold, in particular approximately 4- to 7-fold, molar excess.

The reaction temperature for the ring closure reaction is also within the scope indicated in the above-mentioned patent application, from about −70° to +175° C., the temperatures which are preferred for the short-time variant according to the invention being between about −30° and +100° C.

The ring closure reaction according to the invention is carried out in such a manner that the mass flows of acetoacetamide-N-sulfonic acid or -sulfonate solution and $SO_3$ or $SO_3$ solution, in the appropriate molar ratio of the reactants, are combined and vigorously mixed, the heat of reaction is dissipated, and, after a short hold-up time, the reaction mixture is, where appropriate, passed on for hydrolysis.

Suitable apparatus for the ring closure reaction is, in principle, every apparatus in which it is possible to carry out reactions which take place rapidly and with evolution of heat.

Because of the short reaction time and great evolution of heat, high yields are achieved preferably in special apparatus.

Thus, the special apparatus which is preferably used according to the invention takes the form of particular reactors, where appropriate using evaporation cooling, such as, for example, thin-film reactors with a mechanical agitator, falling film reactors, spray reactors, and tube reactors with or without internal fittings. In a thin-film reactor, for example, the two mass flows are preferably introduced into the reaction chamber separate from one another by being passed either on the wiper axle and jacket or injected at different points on the jacket.

The dissipation of heat can be effected by external cooling and/or by evaporation of the solvent. Since in the absence of external cooling the exothermic reaction causes the temperature to rise to the boiling point of the solvent which is used, the reaction temperature in the case of, for example, methylene chloride, which is preferred as the solvent, is about 40° C. (=boiling point of methylene chloride) at atmospheric pressure. Application of a vacuum can further increase the rate of evaporation and thus the cooling; setting up a particular pressure in the reactor allows the desired reaction temperature to be controlled.

If the ring closure reaction is carried out at a molar ratio of acetoacetamide-N-sulfonic acid or -sulfonate to $SO_3$ of exactly 1:1 no "$SO_3$ adduct" is produced (cf. the reaction diagrams for the ring closure reaction shown above) and it is unnecessary to hydrolyze any adduct. If, however, an excess of $SO_3$ is used—which is the preferred embodiment—then an "$SO_3$ adduct" is produced, and it has to be hydrolyzed.

The reaction product of the ring closure reaction (mainly "$SO_3$ adduct") can be hydrolyzed after temporary storage - which is, where possible, not too long—or immediately after completion of the ring closure reaction; it is preferable for the hydrolysis to take place immediately after the ring closure reaction.

The hydrolysis is generally effected by mixing the reaction product of the ring closure step with water. The amount of water which is added depends on the excess of $SO_3$ used for the ring closure reaction, and its amount is advantageously such that the hydrolysis results in an aqueous $H_2SO_4$ solution of a concentration between about 10 and 90% by weight, preferably from about 50 to 70% by weight.

On investigation of the hydrolysis in detail it has been found that it takes place virtually as rapidly as does the ring closure reaction. Thus, the hydrolysis times are of the same order of magnitude as the reaction times for the ring closure. Hence it is possible to carry out the hydrolysis—as likewise the ring closure reaction—in times not exceeding about 10 minutes, preferably about 0.001 to 60 seconds, in particular in about 0.01 to 10 seconds.

Because of these short hydrolysis times, it is not absolutely necessary to maintain the lowest possible temperatures during the hydrolysis either, so that cooling to a low temperature level is unnecessary for this. With the short hydrolysis times the reaction temperatures are generally between about −10° and +100° C., preferably between about 0° and 50° C. With these there is virtually no risk of any thermal decomposition of the 6-methyl-3,4-dihydro-1,2,3-oxathiazin-4-one 2,2-dioxide which is formed in the hydrolysis.

Because the processes for the ring closure reaction and the hydrolysis take place similarly it is possible advantageously also to carry out the hydrolysis in apparatus of the same type as for the ring closure reaction (thin-film, falling film and spray reactors, flow tubes etc.); however, it is also possible to use normal reaction vessels such as, for example, (stirred) vessels, cascades, etc.

The isolation of the 6-methyl-3,4-dihydro-1,2,3-oxathiazin-4-one 2,2-dioxide from the product solution of the hydrolysis is effected by customary method as are described in, for example, the abovementioned patent application, or the reaction to give the corresponding salts and their isolation is carried out immediately. The yields of the ring closure reaction and hydrolysis are of the same order of magnitude as already indicated in the abovementioned patent application for step (b) of the process described there. However, as a consequence of the short reaction times for the ring closure reaction and the hydrolysis, and the small dimensions of the apparatus used for short-time reactions of this type, there is a considerable increase in the spacetime yields compared with the space-time yields which are obtained by the procedure described in the abovementioned patent application.

It is possible to carry out the hydrolysis in a discontinuous operation; however, a continuous procedure is preferable both for the hydrolysis and for the ring closure reaction.

Some exemplary embodiments of the continuous procedure are shown diagrammatically in the figures.

Figure 1:
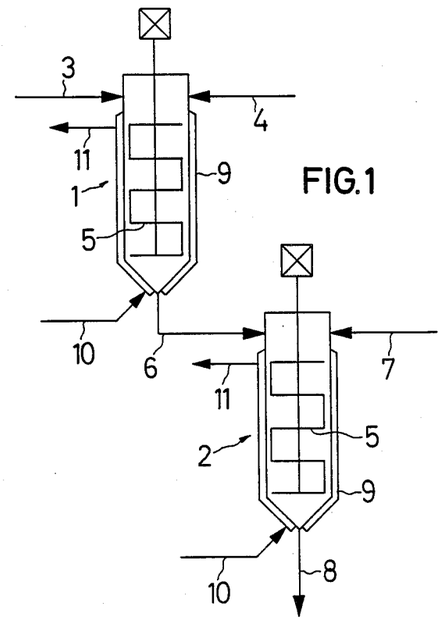

FIG. 1 shows an arrangement of two thin-film reactors 1 and 2 which are connected in series. The solutions of acetoacetamide-N-sulfonic acid or -sulfonate and of $SO_3$ (for example in methylene chloride) are separately metered into the first reactor 1 via lines 3 and 4. A mechanical agitator 5 is used to mix the components vigorously. After the (ring closure) reaction, the product drains via the connection 6 out of the first reactor 1 into the second 2—the hydrolysis reactor. The latter has the same design as the reactor 1 and into it is metered water ($H_2O$) via line 7. The hydrolysis product drains via line 8 and is passed on for working up. Heat dissipation is effected by cooling the reactor walls 9 with a cooling medium via the inlet lines 10 and outlet lines 11.

Figure 2:
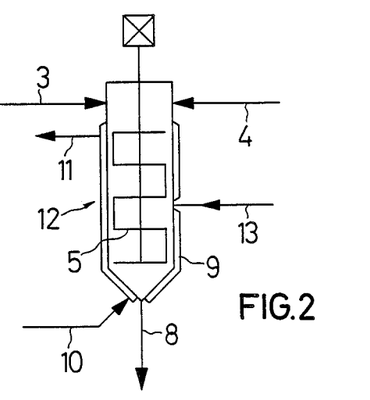

As shown in FIG. 2 both reactions—ring closure reaction and hydrolysis—are carried out in a single thin-film reactor 12 which—in the same way as the two reactors depicted in FIG. 1—is equipped with an agitator 5. In this embodiment the time required for transport of products between the reactors shown in FIG. 1 does not apply. The starting materials acetoacetamide-N-sulfonic acid or -sulfonate and $SO_3$ (dissolved in, for example, methylene chloride) are passed into the upper part of the reactor via lines 3 and 4; after completion of the ring closure reaction the amount of water required for the hydrolysis is introduced via line 13. The heat of reaction which is produced is dissipated in this case also by cooling the reactor wall 9 with a cooling medium via the inlet line 10 and the outlet line 11. The hydrolysis product is removed via line 8.

Figures 3, 4:
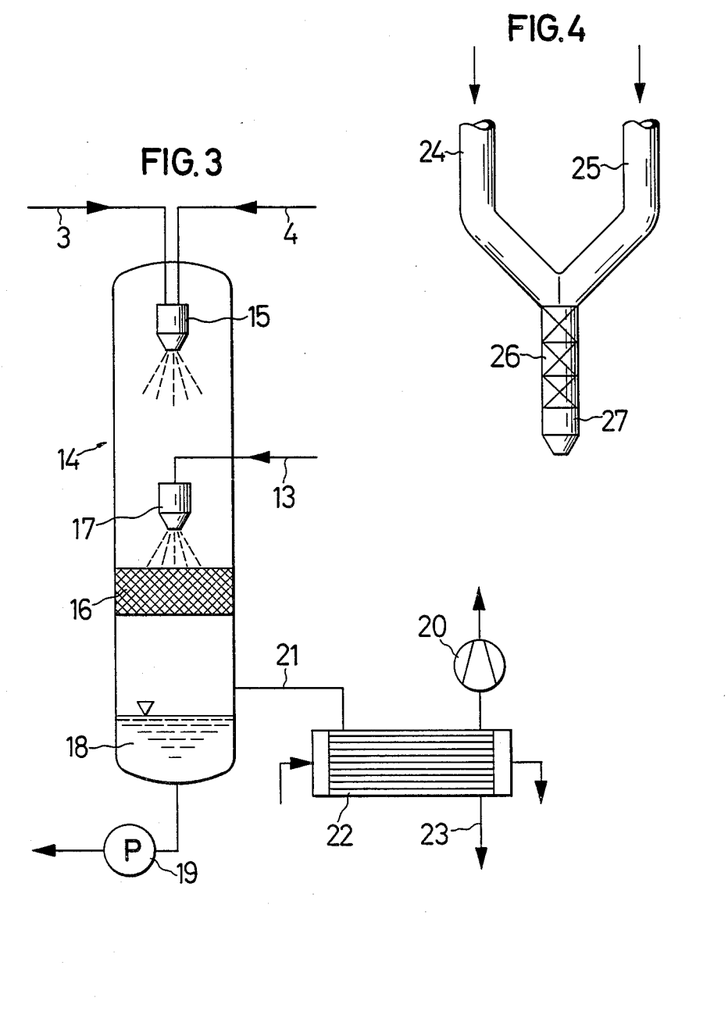

FIG. 3 shows the embodiment of the process according to the invention in a spray reactor 14. The solutions of the starting materials acetoacetamide-N-sulfonic acid or -sulfonate and $SO_3$ are supplied via lines 3 and 4 to the mixing and spray device 15 and are sprayed by this into the reactor. The ring closure product then falls onto the packing 16 onto which water is sprayed through the nozzle 17 for the purpose of hydrolysis; the water is supplied via line 13. At the lower end of the reactor the hydrolysis product 18 is drawn off via the pump 19. The vacuum unit 20, which is connected to the reactor 14 via the line 21 and the condenser 22, generates in the reactor 14 a reduction in pressure to evaporate the solvent. The solvent is condensed in the condenser 22 and drawn off via line 23.

FIG. 4 shows a preferred embodiment of the mixing and spray device 15 depicted in FIG. 3. The starting materials are supplied via lines 24 and 25 and are mixed with static mixers or jet mixers 26 in fractions of a second and are dispersed into drops by the nozzle 27.

The examples which follow are intended to illustrate the invention further.

EXAMPLE 1

Continuous ring closure reaction and hydrolysis in two thin-film reactors in series.

Preparation of the starting solutions:

Acetoacetamide-N-sulfonate:

97.1 g (1.0 mol) of amidosulfonic acid were suspended in 1.0 l of methylene chloride. While agitating, 106 g (1.05 mol) of triethylamine were added, the amidosulfonic acid dissolving as the triethylammonium salt. After addition of 6 g (0.1 mol) of glacial acetic acid, 93.8 g (1.08 mol) of 97% pure diketene were added dropwise, with agitation at an internal temperature of 15° C., within one hour. According to chromatographic analysis, the yield of triethylammonium acetoacetamide-N-sulfonate was 90%. The solution thus obtained was used immediately for the further reaction.

$SO_3$:

183 g of $SO_3$ (2.29 mol) were dissolved in 1070 g of methylene chloride.

Thin-film reactors:

Commercially available laboratory thin-film evaporators of effective length 22 cm and area 160 cm$^2$ were used. The reactors were arranged as shown in FIG. 1.

In the first thin-film reactor, at a temperature of the cooling medium of −8° C. and within one hour, 728 g of the acetoacetamide-N-sulfonate solution prepared as described above (containing 0.4 mol of the sulfonate) were pumped onto the axle of the wiper and, at the same time, the solution of $SO_3$ described above was pumped onto the reactor jacket. The agitator rotated at 1,000 revolutions/minute. The reaction product drained at a temperature of 0° C. out of the first reactor into the hydrolysis reactor and was hydrolyzed there at 0° C. For this purpose, 200 ml of $H_2O$ were pumped in within one hour.

The product emerging from the hydrolysis reactor was worked up by separating off the organic phase and extracting the aqueous phase, containing sulfuric acid, twice more with 1 L of methylene chloride each time. The combined organic phases were dried over sodium sulfate, and the methylene chloride was removed in vacuo. The residue was dissolved in the same amount by weight of methanol, and the pH was then adjusted to 8 to 10 with 20% strength KOH/methanol. The precipitated Acesulfame K was filtered off and dried in vacuo.

The yield was 60.3 g (0.3 mol) =75% based on acetoacetamide-N-sulfonate.

The product hold-up time in the reactors was about 4.2 sec./reactor. The space-time yield calculated from the volume flows of the starting solutions, the Acesulfame K obtained and the reactor dimensions is 325 g of Acesulfame K/l.h.

EXAMPLE 2:

Ring closure reaction and hydrolysis carried out in one and the same (thin-film) reactor as shown in FIG. 2

The amounts of the reactants indicated in Example 1 were fed into a thin-film reactor of the type and dimensions described in Example 1, with the temperature of the cooling medium being −8° C. At the same time, as depicted in FIG. 2, the water for the hydrolysis was pumped in via a connector attached at the center of the reactor.

After working up as in Example 1, Acesulfame K was isolated in a yield of 74% based on acetoacetamide-N-sulfonate.

The product hold-up time was about 2 seconds in both the ring closure and the hydrolysis zones.

The space-time yield calculated from the volume flows of the starting solutions, the Acesulfame K obtained and the reactor dimensions is 640 g of Acesulfame K/l.h.

EXAMPLE 3

The ring closure reaction carried out in a thin-film reactor and the hydrolysis carried out in a roundbottomed flask.

A thin-film reactor of the type and dimensions described in Example 1 was used for the ring closure reaction. The hydrolysis was carried out in a roundbottomed flask which contained water and was located beneath the reactor.

A 0.41 molar acetoacetamide-N-sulfonate solution and a 7.5% (by weight) solution of $SO_3$ in methylene chloride were used. Both starting solutions were pre-cooled to −30° C. The temperature of the cooling medium for the thin-film reactor was −36° C.

The hydrolysis was carried out at 0° C.

The details and results of a few different trial runs are shown in the table below. The hold-up times in the thin-film reactor were calculated from measurements of the product volume contained in the reactor and of the volume flow.

TABLE

| Test | Throughput of acetoacetamide-N—sulfonate solution (mol/min) | Through put of $SO_3$ solution (mol/min) | Yield of Acesulfame K (%) | Hold-up time in the thin-film reactor (sec.) |
|---|---|---|---|---|
| a | 0.1/40 | 0.57/40 | 76 | 5.7 |
| b | 0.1/20 | 0.57/20 | 76 | 2.8 |
| c | 0.1/12.5 | 0.57/12.5 | 75 | 1.8 |
| d | 0.1/10 | 0.57/10 | 75 | 1.4 |

TABLE-continued

| Test | Throughput of acetoacetamide-N—sulfonate solution (mol/min) | Through put of SO₃ solution (mol/min) | Yield of Acesulfame K (%) | Hold-up time in the thin-film reactor (sec.) |
|---|---|---|---|---|
| e | 0.1/4 | 0.57/4 | 70 | 0.7 |
| f | 0.1/2 | 0.57/2 | 70 | 0.3 |

EXAMPLE 4

Ring closure reaction carried out in a thin-film reactor and hydrolysis carried out in a round-bottomed flask with evaporation cooling in vacuo A thin-film reactor of the type and dimensions described in Example 1 was used for the ring closure reaction.

The hydrolysis was carried out in a round-bottomed flask which contained water and was located beneath the reactor. The vacuum was applied via the hydrolysis vessel.

The starting solutions described in Example 1 were used in the ratio of amounts indicated there. The details and results of a few different trial runs are shown in the table below.

TABLE

| Test | Pressure (mbar) | Drain temp. (°C.) | Throughput based on acetoacetamide-N—sulfonate (mol/min) | Yield of Acesulfame K (%) | Hold-up time in the thin-film reactor (sec.) |
|---|---|---|---|---|---|
| a | 35 | −30 | 0.2/30 | 78 | 5.6 |
| b | 100 | −10 | 0.2/29 | 72 | 5.5 |
| c | 100 | −10 | 0.2/6.25 | 75 | 1.2 |
| d | 180 | 0 | 0.2/30 | 68 | 5.6 |
| e | 180 | 0 | 0.2/9.75 | 70 | 1.9 |
| f | 180 | 0 | 0.2/5.5 | 70 | 1.1 |
| g | 180 | 0 | 0.2/3 | 73 | 0.5 |
| h | 180 | 0 | 0.2/2 | 74 | 0.4 |

EXAMPLE 5:

Ring closure reaction and hydrolysis carried out in two thin-film reactors arranged in series as shown in FIG. 1

A 17% (by weight) solution of acetoacetamide-N-sulfonate and a 16% (by weight) solution of SO₃ in methylene chloride were precooled to −25° C. The acetoacetamide-N-sulfonate solution was metered at a rate corresponding to 48 mole of acetoacetamide-N-sulfonate/hour, and the SO₃ solution was metered at a rate corresponding to 288 mole of SO₃/hour, into the first reactor (Sambay type) whose walls were cooled with brine likewise at <25° C. The circumferential velocity of the wiper was 2.2 m/sec.

The product leaving the first reactor was immediately introduced into the second reactor—together with 28 kg of H₂O at room temperature/hour. The circumferential velocity of the wiper in this reactor was the same as in the first reactor.

The product leaving the second reactor was worked up by separating off the organic phase from the aqueous phase containing sulfuric acid at 0 to 5° C., extraction once more of the aqueous/sulfuric acid phase with methylene chloride, drying of the combined organic phases over Na₂SO₄ and removal of the methylene chloride in vacuo, dissolution of the residue in the same amount by weight of methanol and then addition of 20% strength KOH/methanol to pH 8-10. The precipitated Acesulfame K was filtered off and dried in vacuo. The reaction yield was 73% of theory.

The product hold-up time in the ring closure reaction in the first reactor was 5 seconds at film thicknesses of 1 mm.

EXAMPLE 6

Ring closure reaction carried out in a spray reactor and hydrolysis carried out in a stirred flask In a glass tube (internal diameter 10 mm) with static mixers fitted inside, equal volume flows of a 0.7 molar (about 15% strength) solution of acetoacetamide-N-sulfonate and a 4.2 molar (about 23% strength SO₃ solution in methylene chloride were continuously mixed and sprayed into a stirred flask. Hydrolysis was carried out in the stirred flask by continuous supply of water. The heat of reaction was dissipated for the ring closure reaction and for the hydrolysis by evaporation cooling at 40° C. The product hold-up time in the ring closure reaction was about 0.05 seconds. After working up as in Example 1, a yield of Acesulfame K of 67% was obtained.

The calculated space-time yield was 3000 kg of Acesulfame K/h.l.

We claim:

1. A process for the preparation of 6-methyl-3,4-dihydro1,2,3-oxathiazin-4-one 2,2-dioxide which comprises ring closure of acetoacetamide-N-sulfonic acid or one of its salts - dissolved in an equimolar amount to 20-fold molar excess of SO₃ at a temperature of from −70° C. to +175° C. in a reactor within a reactor hold-up time not exceeding 10 minutes after which the ring closure product is passed on out of the reactor or, in the case where more than the equimolar amount of SO₃ is used, the SO₃ adduct of the ring closure product is passed on for hydrolysis, to yield the 6-methyl-3,4-dihydro-1,2,3-oxathiazin-4-one 2,2-dioxide.

2. The process as claimed in claim 1, wherein the reactor hold-up time is 0,001 to 60 seconds.

3. The process as claimed in claim 1, wherein the reactor hold-up time is 0,01 to 10 seconds.

4. The process as claimed in claim 1, wherein the ring closure is carried out at a temperature of from −30 to +100° C.

5. The process as claimed in claim 1, wherein the SO₃ is additionally dissolved in an inert solvent.

6. The process as claimed in claim 1, wherein the SO₃ is dissolved in the same inert solvent as is used for dissolving acetoacetamide-N-sulfonic acid or one of its salts.

7. The process as claimed in claim 1, wherein the salt of acetoacetamide-N-sulfonic acid is selected from the group comprising salts of lithium, ammonium, mono-, di and trialkylammonium, alkali metals and alkaline earth metals.

8. The process as claimed in claim 1, wherein triethylammonium acetoacetamide-N-sulfonate is used.

9. The process as claimed in claim 1, wherein the inert solvent is a chlorinated aliphatic hydrocarbon.

10. The process as claimed in claim 9, wherein the solvent is methylene chloride.

11. The process as claimed in claim 1, wherein the ring closure reaction is carried out in a thin-film, falling film or spray reactor or in a flow tube with or without fittings inside.

12. The process as claimed in claim 1, wherein the heat liberated in the ring closure reaction is dissipated by evaporation of the solvent.

13. The process as claimed in claim 1, wherein more than equimolar amount of $SO_3$ is used, based on the amount of acetoacetamide-N-sulfonic acid, and the hydrolysis is carried out at -10 to +100° C.

14. The process as claimed in claim 13, wherein a 3- to 10-fold molar excess of $SO_3$ is used.

15. The process as claimed in claim 13, wherein the hydrolysis is carried out immediately after completion of the ring closure reaction and in a reactor within a reactor hold-up time not exceeding 10 minutes.

16. The process as claimed in claim 15, wherein the holdup time of the reactor for the hydrolysis is 0.001 to 60 seconds.

17. The process as claimed in claim 15, wherein the holdup time is 0.01 to 10 seconds.

18. The process as claimed in claim 15, wherein the hydrolysis is carried out in an apparatus of the same type as the ring closure reaction.

19. The process as claimed in claim 13, wherein the ring closure and hydrolysis are carried out continuously.

20. The process for the preparation of a salt of 6-methyl-3,4-dihydro-1,2,3-oxathiazin-4-one 2,2-dioxide which comprises reacting the product obtained according to claim 1 with a base.

* * * * *